United States Patent
Minagi et al.

(10) Patent No.: US 9,707,063 B2
(45) Date of Patent: Jul. 18, 2017

(54) DENTAL DIAGNOSIS DEVICE AND DENTAL DIAGNOSIS PROBE

(71) Applicant: National University Corporation Okayama University, Okayama (JP)

(72) Inventors: Shogo Minagi, Okayama (JP); Kazuhiro Oki, Okayama (JP); Yohei Kumazaki, Okayama (JP); Shuichi Wakimoto, Okayama (JP); Koichi Suzumori, Okayama (JP); Kurumi Yagi, Okayama (JP)

(73) Assignee: NATIONAL UNIVERSITY CORPORATION OKAYAMA UNIVERSITY, Okayama (JP)

( * ) Notice: Subject to any disclaimer, the term of this patent is extended or adjusted under 35 U.S.C. 154(b) by 377 days.

(21) Appl. No.: 14/388,368

(22) PCT Filed: Mar. 29, 2013

(86) PCT No.: PCT/JP2013/059670
§ 371 (c)(1),
(2) Date: Sep. 26, 2014

(87) PCT Pub. No.: WO2013/150986
PCT Pub. Date: Oct. 10, 2013

(65) Prior Publication Data
US 2015/0072312 A1    Mar. 12, 2015

(30) Foreign Application Priority Data
Apr. 2, 2012   (JP) ................................. 2012-084339

(51) Int. Cl.
*A61C 19/00*   (2006.01)
*A61C 19/05*   (2006.01)

(52) U.S. Cl.
CPC .................................... *A61C 19/05* (2013.01)

(58) Field of Classification Search
CPC ........... A61C 19/05; A61B 7/003; A61B 7/04; A61B 5/0051; A61B 5/4827;
(Continued)

(56) References Cited

U.S. PATENT DOCUMENTS

| | | | |
|---|---|---|---|
| 5,730,151 A | * | 3/1998 | Summer ................ A61C 19/05 600/587 |
| 2009/0274325 A1 | * | 11/2009 | Abolfathi ............ H04R 25/554 381/151 |

FOREIGN PATENT DOCUMENTS

| | | |
|---|---|---|
| JP | 58-10713 | 1/1983 |
| JP | 58-46312 | 3/1983 |

(Continued)

OTHER PUBLICATIONS

Shigeki Sugisaki, et al., "Evaluation of functional condition of occlusion by time-frequency analysis of occlusal sound signal", Journal of the Acoustical Society of Japan, 1991, vol. 47, No. 10, pp. 749 to 753, 5 pages—English, 5 pages—Japanese.

(Continued)

*Primary Examiner* — Cris L Rodriguez
*Assistant Examiner* — Mirayda A Aponte
(74) *Attorney, Agent, or Firm* — Andrew F. Young, Esq.; Lackenbach Siegel, LLP

(57) ABSTRACT

A dental diagnosis device has an occlusion sound detection member that detects occlusion sounds by teeth and an analysis member that analyzes the teeth occlusion based on detected occlusion sounds by the occlusion detection member. The occlusion detection member comprises a sucker shaped suction member that sticks to a tooth, a hollow passage connected to a through-hole installed in the suction member and it is operably controlled to appropriate negative pressure by which the suction member is adhered to a tooth, and a detection member connected to the suction member, which detects occlusion sound via the suction member.

3 Claims, 7 Drawing Sheets

(58) Field of Classification Search
CPC ..... A61B 5/4824; A61B 5/0537; A61B 5/053; A61B 5/4872; A61B 5/4528; A61B 5/103; A61B 5/0053; A61B 5/1076; A61B 5/107
USPC .......... 433/25; 600/552, 553, 571, 547, 586, 600/587
See application file for complete search history.

(56) References Cited

FOREIGN PATENT DOCUMENTS

| | | |
|---|---|---|
| JP | 58-69533 | 4/1983 |
| JP | 58-221931 | 12/1983 |

OTHER PUBLICATIONS

International Search Report, PCT Appln. Serial No. PCT/JP2013/059670 mailed May 14, 2013, 3 pages—Japanese; 2 pages—English.
Shigeki Sugisaki, et al., "Evaulation of functional condition of occlusion by time-frequency analysis of occlusal sound signal", Journal of the Acoustical Society of Japan, 1991, vol. 47, No. 10, pp. 749 to 753.
Harumi Wakuda, et al., "Clinical Usage of Dental Sound Checker: Occlusal adjustment of prosthesis on loss of many teeth", Kyushu Shika Gakkai Zasshi, 1982, vol. 36, No. 5, pp. 848 to 854.

* cited by examiner

DENTAL DIAGNOSIS DEVICE AND DENTAL DIAGNOSIS PROBE

CROSS REFERENCE TO RELATED APPLICATIONS

This application claims priority from International Ser. No. PCT/JP2013/059670 filed Mar. 29, 2013 the entire contents of which are incorporated herein by reference, which in turn claims priority to Japanese Application Ser. No. 2012-084339 filed Apr. 2, 2012, the entire contents of which are incorporated herein by reference.

FIGURE SELECTED FOR PUBLICATION

FIG. 1

BACKGROUND OF THE INVENTION

Field of the Invention

The present invention relates to a dental diagnosis device and a dental diagnosis probe and a system for operating the same. More particularly, the present invention provides a technology to assess patient's teeth occlusion with increased accuracy and reliability.

Description of the Related Art

It is important for dental diagnosis to assess precisely specific teeth occlusion to be adjusted when the patient's teeth occlusion (bite) is adjusted.

Conventionally, teeth occlusion is assessed by patient's bite on a red-carbon paper functioning as a so-called occlusion paper. The information obtained by using the occlusion paper is, also unfortunately limited to such position information at teeth occlusion contacting points of both jaws. Accordingly, a practical occlusion adjustment is conducted based on such sensory information of occlusion from the patient and the general finger sensation of the dentist. Further, other than the method using the occlusion paper, a variety of technologies are known to assess teeth occlusion (refer to Non-Patent Document, 1, 2, the contents of which are incorporated herein by reference).

Non-Patent Document 1 discloses a technology to compare the strengths of right and left occlusions by using an acceleration sensor embedded in a headset or by wearing a microphone. Non-Patent Document 2 discloses a technology to assess teeth occlusion by using an acceleration pickup installed to the teeth.

Further, a T-SCAN from Techscan Co. is a device to analyze occlusion contact by biting a pressure-sensitive film having approximately 100 μm thickness. Further, OCCLUSER from GC Co. is a device to analyze occlusion contact by measuring the coloring state of the pressure-sensitive film bitten by a patient, which is the exclusive pressure-sensitive film called a dental press scale.

PRIOR ARTS

Non-Patent Document

Non-Patent Document 1: Clinical Usage of Dental Sound Checker: Occlusal adjustment of prosthesis on loss of many teeth; Harumi Wakuda, Toshihiro Shimizu, Fumitaka Ito, Isao Shinhara, Kiyotaka Sato, Satoshi Kaku, Shizuo Toyoda The Journal of the Kyushu Dental Society 36(5), 848-854, 1982

Non-Patent Document 2: Development of the Premature Contact Diagnosis Equipment Using Palpation: Research on the distribution of peak frequency and the maximum peak value; Makoto Yoshida, Shigemitsu Sakuma, Yutaka Ito, Yoshihisa Fujii, Shigeru Sugiyama, Takuya Masuda; The Aichi-Gakuin journal of dental science 40(4), 521-527, 2002-12-31

ASPECTS AND SUMMARY OF THE INVENTION

Unfortunately, it is not possible to exactly assess teeth occlusion using the prior arts.

For example, the difference of strength between right and left occlusion can be understandable only more or less using the art of Non-Patent Document 1 and the accuracy thereby is not enough for adjustment of occlusion. Further, for example, the art disclosed in Non-Patent Document 2 was not used in the clinical practice because of the large size of acceleration pick-up.

Further, it is hard to exactly assess a direct teeth occlusion of the upper jaw and teeth of the lower jaw by the conventional method using the pressure sensitive film because of variable relationship of the occlusion contact due to the intermediate thick pressure sensitive film between teeth of the upper jaw and teeth of the lower jaw.

One aspect of the present invention is conducted to solve one or more of the above problems and one another aspect of the present invention is to provide a dental diagnosis device and a dental diagnosis probe as a system so that the teeth occlusion can be assessed exactly.

Means to Solve the Objects

In one aspect of the present invention, the dental diagnosis device of the present invention to resolve the above problem is characterized by comprising; a occlusion sound detection member that detects occlusion sound occurring by occluding teeth, and an analysis member that analyzes teeth occlusion based on detected occlusion sound detected by the occlusion detection member; wherein said occlusion sound detection member is connected to a sucker-like suction member to stick to a tooth and a through-hole installed to the suction member; a hollow-like pathway controlled to an appropriate level of negative pressure at which the suction member can stick to a tooth; a detection member connected to the suction member, which detects occlusion sound via the suction member.

Effects of the Invention

According to the present invention, teeth occlusion can be exactly assessed.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
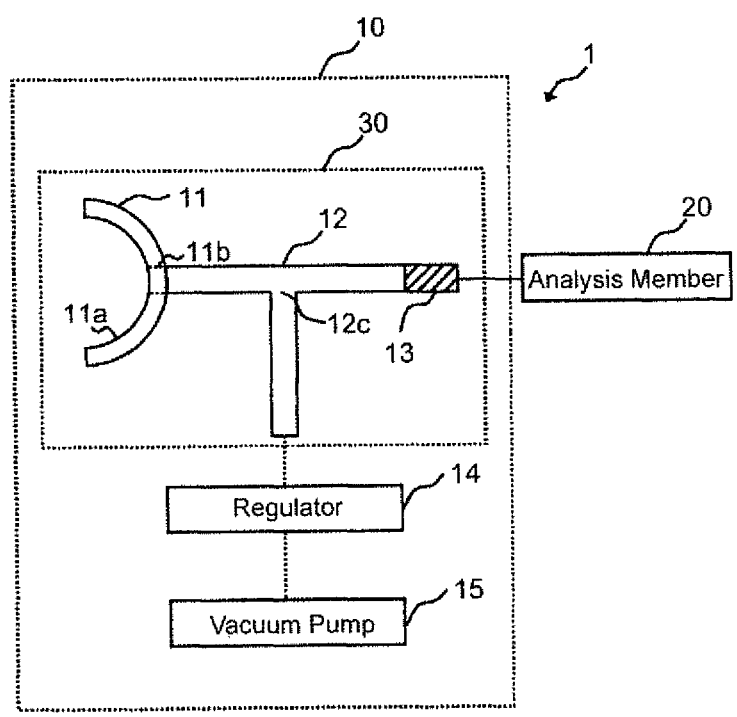
FIG. 1 is a block diagram illustrating a dental diagnosis device of the present embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, or in a manner that may be helpful in understanding embodiments of the present invention; however, the order of description should not be construed to imply that these operations are order dependent or a required feature.

The present invention provides a system to assess exactly teeth occlusion by using a structure including; an occlusion sound detection member that detects occlusion sound or teeth vibration taking place when teeth are brought into occlusion (hereinafter collectively just "occlusion sound") an analysis member that analyzes teeth occlusion based on detected occlusion sound by the occlusion detection member.

FIG. 1 is a block diagram illustrating a dental diagnosis device of the present embodiment.

Referring to FIG. 1, a dental diagnosis device of the present embodiment comprises; an occlusion sound detection member 10 that detects occlusion sound occurring by occluding teeth, and an analysis member 20 that analyzes teeth occlusion based on detected occlusion sound by the occlusion detection member. Further, the occlusion sound detection member 10 includes a dental diagnosis probe 30, a regulator 14 and a vacuum pump 15. Further, the dental diagnosis probe 20 includes a suction member 11, a tube 12 and a microphone 13.

Further, despite drawing one dental diagnosis probe 30 in FIG. 1, a dental diagnosis device or system 1 may include 1 or a plurality of dental diagnosis probes 30. For example, in the case of the dental diagnosis device 1 having sixteen (16) dental diagnosis probes 30, each dental diagnosis probe 30 can be mounted on each tooth of the upper jaw. Hereinafter, the inventor illustrates each structural element of a dental diagnosis device 1.

A suction member 11 having curved suction surface 11a that sticks to patient's tooth is a suction member (a suction mechanism or means operable with a suction) constituted from e.g. silicone rubber material. A through-hole 11b is formed in the approximately center of the suction member 11. The suction member 11 is connected to a tube 12 through the through-hole 11b.

Further, a size of a suction member 11 and a curvature of curved suction surface 11a may be variable in accordance with patient's small-and-large tooth and a curvature thereof. Further, a suction member 11 can be made of partially different material. For example, if a harder material is used for surrounding area, a center side of the suction member 11, of the through-hole 11b and outer side thereof can be made of a softer material, the occlusion sound occurred around the teeth is more effectively transferred to the inside of the tube 12.

A tube 12 is a hollow cylinder-like air passage connected to a suction member 11 and can be made of silicone rubber and so forth. The tube 12 connected to a microphone 13 functions as a transmission path for transmission of occlusion sound occurred on the tooth to which a suction member 11 sticks. Further, the tube 12 includes a bifurcation member 12c that bifurcates in the middle. For example, the bifurcation tube 12 is a passage having a smaller diameter than the diameter of the main tube 12. The bifurcation member 12c of the tube 12 is connected to a vacuum pump 15 via a regulator 14. Then, the inside pressure of the tube 12 is controlled to the adequate level of negative pressure by which the suction member 11 can stick to a tooth. Accordingly, the tube 12 functions also as a sticking control means by which the suction member 11 is stuck to a tooth.

A microphone 13 functions as a detection member (detection means) to detect the transmitted occlusion sound via the tube 12, i.e. air vibration inside the tube 12, The microphone 13 connected to batteries, not shown in Fig, works by such batteries.

The regulator 14 is a device to control an action of the vacuum pump 15. The vacuum pump 15 is a device to let the air pressure inside the tube 12 be negative. Further, since if the inside of the tube 12 is under absolute vacuum, no sound transmits inside the tube 12; the inside of the tube 12 is controlled during an operational use to be, for example, at midway between normal pressure and absolute vacuum to provide an effective suction.

An analysis member 20 analyzes teeth occlusion based on detected occlusion sound by the occlusion detection member 10. The analysis member 20 is, for example, an oscilloscope to display the pattern of electrical signals of occlusion sound detected by the microphone 13. Further, an analysis member 20 can be, for example, an A/D converter that digitizes electrical signals of occlusion sound detected by a microphone 13 or a normal computer device containing suitable process control features that analyzes the data digitized by an A/D converter.

As illustrated, a dental diagnosis device 1 of the present embodiment comprises a simple structure including a occlusion sound detection member 10 that detects occlusion sound occurring by occluding teeth and an analysis member 20 that analyzes teeth occlusion based on detected occlusion sound by the occlusion detection member so that an exact assessment of teeth occlusion can be conducted based on occlusion sound occurred on the patient's teeth occlusion.

Structure of Dental Diagnosis Probe

Figure 2:
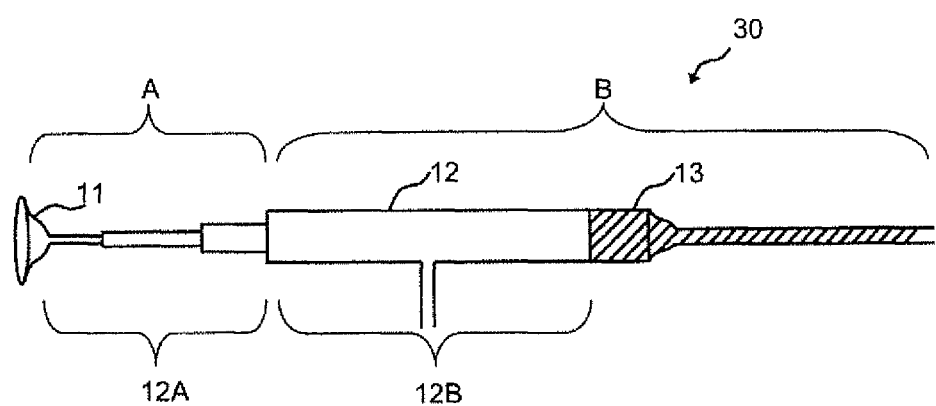
FIG. 2 is a structural drawing illustrating a dental diagnosis probe of the present embodiment.

FIG. 2 is a drawing of structural example illustrating a dental diagnosis probe of the present embodiment. FIG. 2 is a magnified drawing of the dental diagnosis probe 30 in FIG. 1, illustrating further specifically.

A tube 12 of the dental diagnosis probe 30 illustrated in FIG. 2 comprises the tube front part 12A located at the tip side that is the side at which the suction member 11 is installed, and the tube back part 12B located at the back side that is the side at which the microphone 13 is installed. The tube front part 12A has a structure in which the cross section diameter becomes gradually larger toward the tube back part 12B and the passage diameter (inner diameter) also becomes larger. Further, the tube front part 12A can be a tapering shape toward the suction member 11, wherein the cross section diameter becomes gradually smaller.

According to an embodiment illustrated in FIG. 2, the cross section diameter of the tube front part 12A varies in three steps. Each cross section diameter of the first step, the second step and the third step is respectively e.g. approximately 0.5 mm, 1 mm and 2 mm. Further, the length of the tube front part 12A in the axis direction is e.g. approximately 2 cm. On the other hand, the cross section diameter and the length in the axis direction of the tube back part 12B are respectively approximately 5 mm and 3 cm. Further, the suction member 11 has approximately 2 mm width and approximately 5 mm height. Further, above each numerical number is one example and the present invention is not limited to such each number.

Accordingly, the cross section diameter varies along the axis direction of tube 12 so that a small diameter inside the mouth can reduce the load on the patient and a large diameter outside of the mouth can cut the time needed to obtain the negative pressure inside the tube 12.

Referring to a dental diagnosis probe 30 illustrated above, the part shown as region A, i.e. the suction member 11 and the tube front part 12A, are set inside the patient's month. On the other hand, the part shown as region B, i.e. the tube back part 12B, and the microphone 13 are set outside the patient's mouth. The part shown as the region A is removable from the tube 12 or sterilizable. Accordingly, not only the region A adjustable from patient to patient should be replaced to be usable but also sanitation thereof can be assured. Further, the region A is less expensive than the previously described pressure film so that the dental diagnosis of teeth occlusion can be done at low cost.

In addition, it is preferable that the region A can be bent so that the opening direction of the suction member 11 can be structurally in the predetermined angle (e.g. 90 degree) from the tube 12. Accordingly, a dental diagnosis probe 30 can be mounted on each patient's tooth in a convenient use manner.

Mounting Embodiment of Dental Diagnosis Probe

Figure 3:
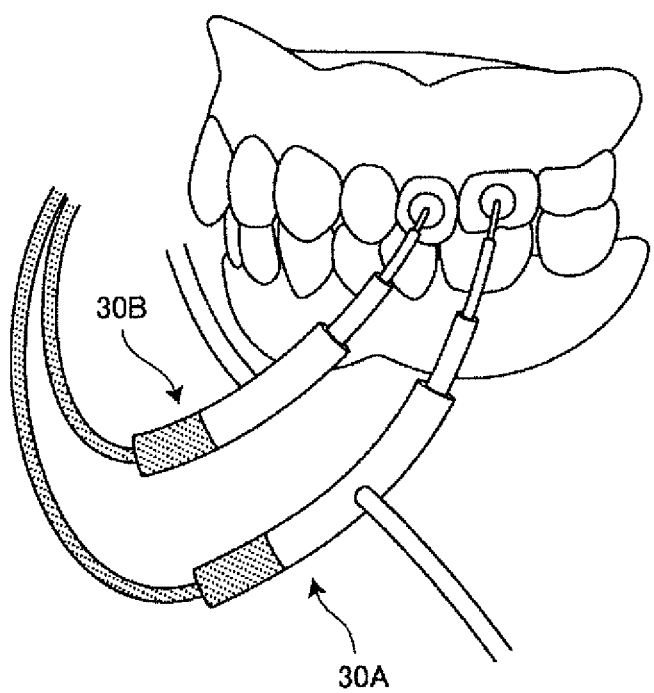
FIG. 3 is a drawing illustrating mounting of a dental diagnosis probe of the present embodiment.

FIG. 3 is a drawing illustrating mounting of a dental diagnosis probe of the present embodiment.

FIG. 3 is illustrating an embodiment wherein two dental diagnosis probes 30A, 30B are mounted as a dental diagnosis probe 30. Further, in a practical dental intervention, for example, a dental diagnosis probe 30 can be mounted on all teeth of patient's upper jaw, i.e. maximum 16 teeth. Of course, a dental diagnosis probe 30 can be mounted on a tooth of patient's lower jaw.

Referring to FIG. 3, in the case of mounting two dental diagnosis probes 30A, 30B, for example, each dental diagnosis probe 30A, 30B is mounted on two adjacent teeth. Accordingly, an occlusion contact state can be analyzed as to the analytical object tooth and the adjacent tooth to the analytical object tooth. Further, two symmetrically positioned teeth can be mounted. In this case, a difference of occlusion contact states can be analyzed as to the analytical object tooth and the symmetrically positioned teeth to the analytical object tooth.

Further, in the case of mounting three dental diagnosis probes, for example, an analytical object tooth, the adjacent tooth to the analytical object tooth and the symmetrically positioned teeth are mounted. Accordingly, an occlusion contact state can be further appropriately analyzed as to the analytical object tooth. Further, only one dental diagnosis probe 30 is mounted to analyze an occlusion slide and an occlusion interference of the tooth per se mounted with a dental diagnosis probe 30.

Embodiment of Structure of Dental Diagnosis Probe Mounting Device

Figure 4:
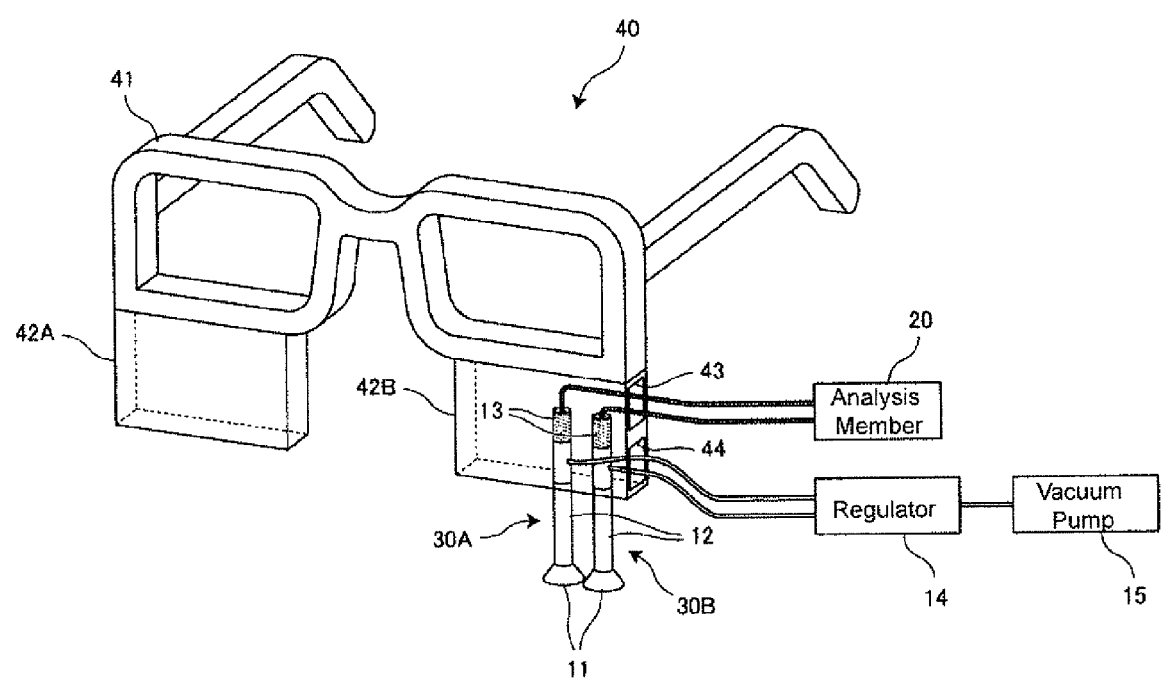
FIG. 4 is a block diagram illustrating a mounting devise of a dental diagnosis probe of the present embodiment.

FIG. 4 is a block diagram illustrating a mounting devise of a dental diagnosis probe of the present embodiment.

FIG. 4 is illustrating one embodiment of a dental diagnosis probe mounting device 40 to mount the above dental diagnosis probe 30 on a practical dental intervention.

Referring to FIG. 4, in the present embodiment, a dental diagnosis probe mounting device 40 includes an eyeglasses-like frame 41 wearable around patient's eyes and base member 42A, 42B, chassis installed under the eyeglasses-like frame 41.

The lower face of the base member 42A, 42B are open so that maximum 8 probes of dental probes 30 can be positioned respectively as to the base member 42A, 42B in an aspect in which the suction member 11 are facing downward. Further, referring to FIG. 4, it is one aspect in which two dental diagnosis probes 30A, 30B are positioned inside the base member 42B for convenience of illustration. As described above, it is preferable that the suction member 11 can be structured having the predetermined angle (e.g. 90 degree) from the tube 12.

A sidewall 43, 44 is installed in the sidewall of base member 42B. A microphone 13 of the dental diagnosis probe 30A, 30B positioned inside the base member 42B is connected to an analysis member installed outside through the sidewall hole 43. Also, the tube 12 of the dental diagnosis probe 30A, 30B is connected to a regulator 14 installed outside through the sidewall hole 44.

When an intervention is conducted using such dental diagnosis probe mounting device 40, a patient wears an eyeglasses-like frame 41 around eyes and a dentist mounts the suction member 11 extending downward from the base member 42A, 42B on patient's tooth or removes the suction member 11 mounted on patient's tooth. Accordingly, the dentist can proceed treatment on patient's tooth while determining teeth occlusion.

Embodiment of Result of Analysis Conducted by Analysis Member

Figure 5A:
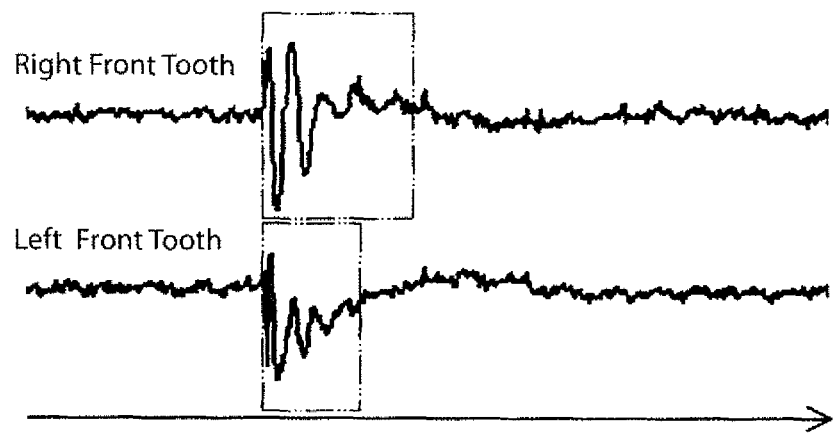
FIG. 5A is a figure illustrating an analytical result conducted by an analysis member of the present embodiment.
Figure 5B:
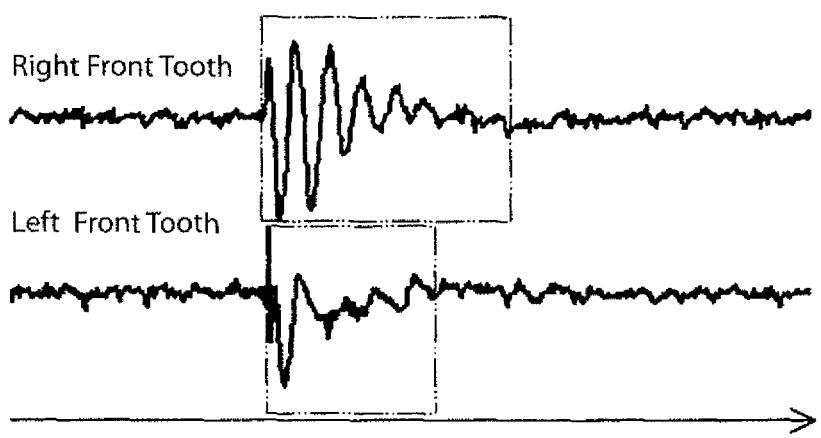
FIG. 5B is a figure illustrating an analytical result conducted by an analysis member of the present embodiment.

FIG. 5A and FIG. 5B are figures illustrating a result of an analysis conducted by an analysis member of the present embodiment. FIG. 5A is the figure illustrating an example pattern of occlusion sound on normal occlusion contact FIG. 5B is the figure illustrating an example pattern of occlusion sound on abnormal occlusion contact.

FIG. 5A and FIG. 5B are illustrating patterns of occlusion sound detected by the analysis member 20 when two dental diagnosis probes 30 are respectively mounted on the right front tooth and the left front tooth, wherein the analysis member 20 is an oscilloscope. In FIGS. 5A and 5B, the horizontal axis is the time and the perpendicular axis is the amplitude of vibration of occlusion sound.

Referring to FIG. 5A, if occlusion contacts are normal, the time of occurrence of occlusion sound on the right tooth and the time of occurrence of occlusion sound on the left tooth coincide virtually. Specifically, the amplitude pattern above a certain level occurs virtually coincidentally. On the other hand, referring to FIG. 5B, if occlusion contacts are abnormal, there is a lag time between the time of occurrence of occlusion sound on the right tooth and the time of occurrence of occlusion sound on the left tooth. Accordingly, it can be found whether it is a normal occlusion contact or an abnormal occlusion contact based on the occurrence timing of occlusion sound, i.e. the timing on which the first pattern having an amplitude above a certain level appears.

Further, referring to FIG. 5A, if occlusion contacts are normal, the time period of occurrence of occlusion sound on the right tooth and the time period of occurrence of occlusion sound on the left tooth are virtually the same period. Specifically, the time periods of occurrence of pattern having a predetermined amplitude or frequency are the same period. On the other hand, referring to FIG. 5B, if occlusion contacts are abnormal, there is a lag between the time period of occurrence of occlusion sound on the right tooth and the time period of occurrence of occlusion sound on the left tooth. According to Embodiment referring to FIG. 5B, the occurrence period of the low-frequency component of occlusion sound on the right from tooth becomes longer. Accordingly, it can be found whether it is a normal occlusion contact or an abnormal occlusion contact based on the occurrence period of occlusion sound.

Accordingly, it can be found whether it is a normal occlusion contact or an abnormal occlusion contact based on the pattern analysis of occlusion sound. Further, the pattern analysis of occlusion sound can be applied to an occlusion interference analysis. According to Embodiment referring to FIG. 5A and FIG. 5B, it is deemed that the occlusion interference occurs on the right front tooth as shown in FIG. 5B. It can be found based on that the occurrence period of pattern having a large amplitude is long and that the occurrence period of low-frequency component is long, and so forth.

Further, referring to FIG. 5A and FIG. 5B, the case in which a dental diagnosis probe is mounted on two teeth is illustrated, whereas, for example, the dental diagnosis probe can be mounted on all teeth of upper jaw. Accordingly, a sequence in which the teeth of upper jaw are contacting to the teeth of lower jaw can be analyzed so that it can be found that occlusion of a crown restoration material is high or low, for example, when the crown restoration material is put on for cavity protection.

Further, referring to FIG. 5A and FIG. 5B, one Embodiment in which a dentist diagnoses based on displayed pattern of occlusion sound on the oscilloscope, when an analysis member 20 is an oscilloscope, is illustrated, but an analysis member 20 can be an A/D converter that digitizes electrical signals of occlusion sound detected by the microphone 13 (referring to FIG. 1) or a normal computer device that analyzes the data digitized by an A/D converter. In this case, the analysis member 20 can analyze whether the occlusion is normal or abnormal and the state of the occlusion contact of each tooth; in accordance with the timing on which the pattern having an amplitude above a certain level as to the pattern of occlusion sound appears, an occurrence period of the pattern due to the amplitude and/or occlusion sound or the time until the occurred pattern attenuates, the difference in between frequency components, and so forth.

Alternative Embodiment of Structure of Dental Diagnosis Device

Figure 6:
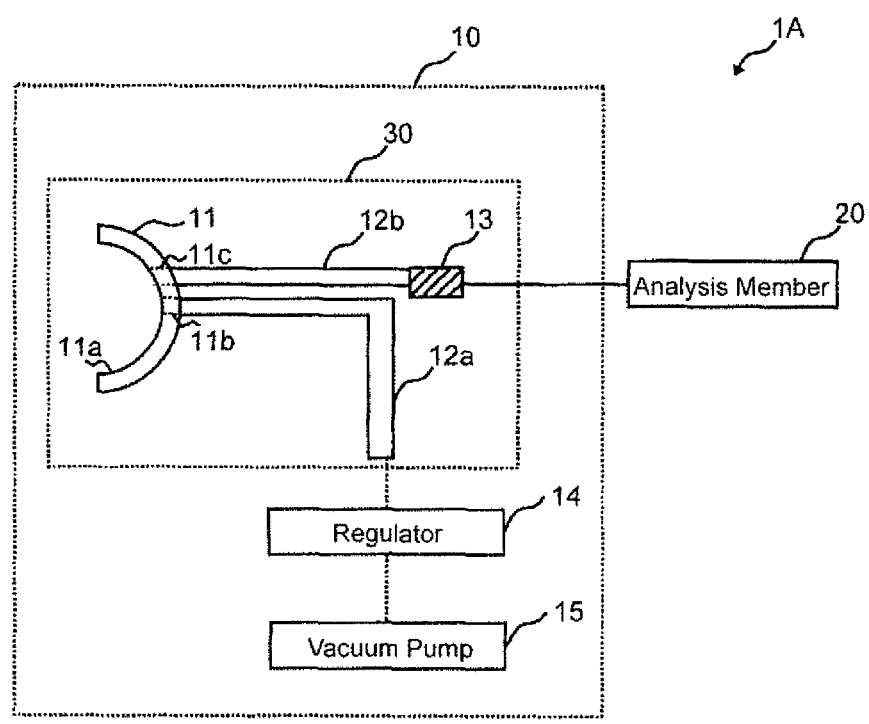
FIG. 6 is a block diagram illustrating the dental diagnosis device of the first alternative embodiment of the present invention.

FIG. 6 is a block diagram illustrating the dental diagnosis device of the first alternative embodiment of the present invention. Hereinafter, the first alternative embodiment of the dental diagnosis device 1 illustrated referring to FIG. 1 is illustrated.

Further, a dental diagnosis device 1A according to the first alternative embodiment is different from the dental diagnosis device referring to FIG. 1 in view of that a tube 12 comprises two tubes 12a and 12b. Referring to FIG. 6, the same element as to the dental diagnosis device 1 referring to FIG. 1 has the same sign and the overlapping illustration is omitted arbitrarily.

Referring to FIG. 6, a suction member 11 having a curved suction surface 11a that sticks to patient's tooth is a suction member (suction means) constituted from e.g. silicone rubber material. A through-hole 11b is formed at the approximate center of the suction member 11 and a through-hole 11c is formed outside the through-hole 11b. The suction member 11 is connected to the tube 12a via one through-hole 11b and connected to 12b via another through-hole 11c. The suction member 11 is removable and sterilizable. Further, a projection protruding toward the tooth side on which the suction member 11 is mounted may be installed at the marginal part of the through-hole 11b on the suction surface 11a. Accordingly, an enclosed space between the tooth and the projection is created so that the air inside the tube 12b needed to transmit occlusion sound can be ensured and maintained even when the suction strength is increased by increasing the negative pressure on the suction member 11.

A tube 12a is a hollow cylinder-like air passage connected to a suction member 11 and can be made of silicone rubber and so forth. The tube 12a is connected to a vacuum pump 15 via a regulator 14. Then, the inside pressure of the tube 12a is controlled to the adequate level of negative pressure by which the suction member 11 can stick to a tooth. Accordingly, the tube 12a functions also as a sticking control means by which the suction member 11 is stuck to a tooth.

On the other hand, a tube 12b is a hollow cylinder-like tube connected to a suction member 11 and can be made of silicone rubber and so forth. The tube 12b connected to a microphone 13 functions as a transmission path for transmission of occlusion sound occurred on the tooth to which a suction member 11 is sticking.

A microphone 13 functions as a detection member (detection means) to detect the transmitted occlusion sound via the tube 12b, i.e. air vibration inside the tube 12b. The microphone 13 connected to batteries, not shown in Fig., works by such batteries.

The regulator 14 is a device to control a performance of the vacuum pump 15. The vacuum pump 15 is a device to let the air pressure inside the tube 12a be negative.

As illustrated above, a dental diagnosis device 1A according to the first alternative embodiment is different from a dental diagnosis device referring to FIG. 1, wherein the device 1A includes two tubes 12, i.e. the tube 12a and the tube 12b. Accordingly, detection of occlusion sound and sticking of the suction member 11 to a tooth can be controlled respectively independently.

Second Alternative Embodiment of Dental Diagnosis Device

Figure 7:
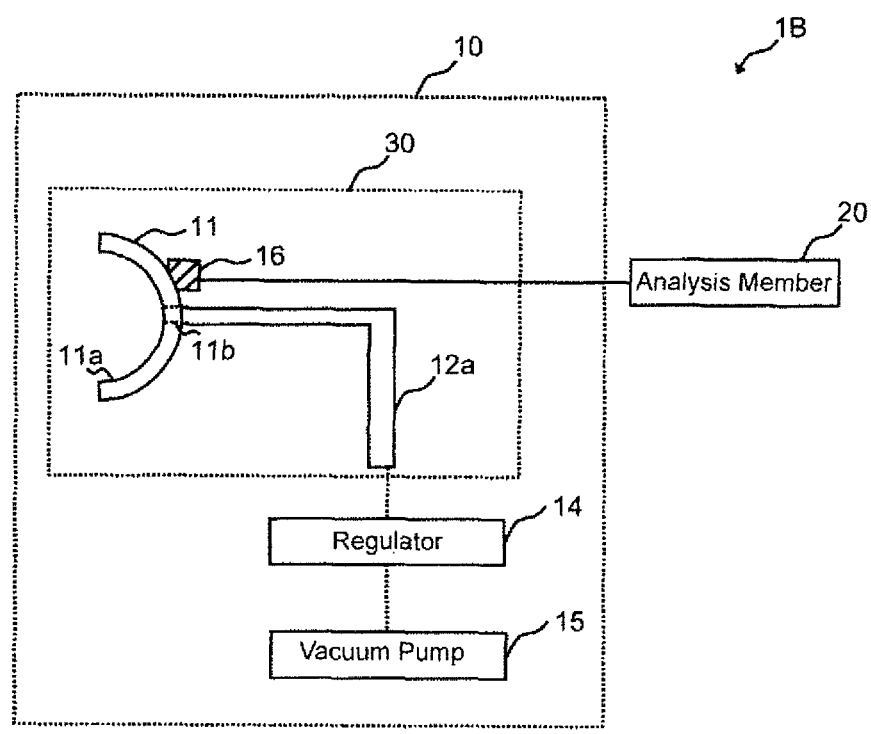
FIG. 7 is a block diagram illustrating the dental diagnosis device of the second alternative embodiment of the present invention.

FIG. 7 is a block diagram illustrating the dental diagnosis device of the second alternative embodiment of the present invention. Hereinafter, the alternative embodiment of the dental diagnosis device 1A illustrated referring to FIG. 6 is illustrated.

Further, a dental diagnosis device 1B according to the second alternative embodiment is different from a dental diagnosis device 1A referring to FIG. 6 in view of comprising a vibration sensor (acceleration sensor) 16 instead of a tube 12b and a microphone 13. Referring to FIG. 7, the same element as to a dental diagnosis device 1 referring to FIG. 1 and a dental diagnosis device 1A referring to FIG. 6 has the same sign and the overlapping illustration is omitted arbitrarily.

Referring to FIG. 7, a suction member 11 having a curved suction surface 11a that sticks to patient's tooth is a suction member (suction means) constituted from e.g. silicone rubber material. A through-hole 11b is formed in the approximately center of the suction member 11. The suction member 11 is connected to a tube 12a through the through-hole 11b. The suction member 11 is removable and sterilizable. Further, a vibration sensor 16 to detect vibration of the suction member 11 is mounted to the suction member 11.

The tube 12a is a hollow cylinder-like air passage connected to the suction member 11 and can be constituted from e.g. silicone rubber material. The tube 12a is connected to a vacuum pump 15 via a regulator 14. Then, the inside pressure of the tube 12a is controlled to the adequate level of negative pressure by which the suction member 11 can stick to a tooth.

The regulator 14 is a device to control a performance of the vacuum pump 15. The vacuum pump 15 is a device to let the air pressure inside the tube 12a be negative.

As illustrated above, a dental diagnosis device 1B according to the second alternative embodiment is different from a dental diagnosis device 1A referring to FIG. 6 in view of comprising a vibration sensor (acceleration sensor) 16 instead of a tube 12b and a microphone 13 so that the detection and the analysis of occlusion sound can be conducted by a simpler structure than a diagnosis device 1A according to the first alternative embodiment.

As illustrated above, according to a dental diagnosis device and a dental diagnosis probe of the present embodiment, a pressure sensitive film having thickness to be intervened between teeth of upper and lower jaws is not needed so that the actual contact between teeth of upper and lower jaws can be assessed and diagnosed as is. Specifically, for example, actual sequence, strength and existence-or-nonexistence of slide as to contact occurred between teeth of upper and lower jaws can be assessed independently for an individual tooth. Further, a dental diagnosis device and a dental diagnosis probe according to the present embodiment can be applied to the adjustment of occlusion when a crown restoration material is put on as a dental treatment.

Now the present invention is illustrated in detail referring to Figs, the present invention is not limited to such specific structures and may include a variety of alternations and equivalent structures without departing the scope of claims of the present invention.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE DESIGNATOR LISTING

1 Dental diagnosis device
10 Occlusion sound detection member
11 Suction member (Stick member)
11a Suction surface
11b Through-hole
12 Tube (Passage)
12a Tube (First passage)
12b Tube (Second passage)
13 Microphone (Detection member)
14 Regulator
15 Vacuum pump
16 Vibration sensor (detection member)
20 Analysis member
30 Dental diagnosis probe

What is claimed is:

1. A dental diagnosis device for determining a teeth occlusion for a plurality of teeth, comprising:
   an occlusion sound detection member that detects an occlusion sound occurred by said teeth occlusion, and
   an analysis member that analyzes said teeth occlusion based on said occlusion sound detected by said occlusion detection member, wherein:
   said occlusion sound detection member further comprises:
      a sucker shaped suction member that sticks to at least one of said teeth,
      a hollow passage connected to a through-hole installed in said sucker shaped suction member and controlled to an appropriate negative pressure by which said sucker shaped suction member can be stuck to a selected tooth, and
      a detection member that is connected to said sucker shaped suction member detects said occlusion sound via said sucker shaped suction member;
   said analysis member finds whether an occlusion contact is normal or abnormal based on at least one of a time of occurrence, an amplitude and a frequency of occlusion sound detected by said occlusion sound detection member; and
   said occlusion sound detection member further comprises:
      a vacuum pump in order to control said hollow passage to negative pressure, and
      a regulator to control a performance of said vacuum pump.

2. The dental diagnosis device according to claim 1 is characterized in that, wherein:
   said hollow passage functions also as a transmittance pathway of occlusion sound occurred on said teeth, and
   said detection member detects the occlusion sound transmitted through said hollow passage.

3. A dental diagnosis probe to detect an occlusion sound occurring upon a teeth occlusion, comprising:
   a sucker shaped suction member that sticks to said teeth,
   a hollow passage connected to a through-hole installed in said sucker shaped suction member and controlled to an appropriate negative pressure by which said sucker shaped suction member can be stuck to a tooth;
   a detection member that is connected to said sucker shaped suction member and detects said occlusion sound via said suction member;
   wherein:
   said passage functions also as a transmittance pathway of occlusion sound on said teeth, and
   said detection member detects the transmitted sound through said passage.

* * * * *